United States Patent [19]
Walsh et al.

[11] Patent Number: 5,300,018
[45] Date of Patent: Apr. 5, 1994

[54] APPLICATOR MEANS FOR THE APPLICATION OF ANESTHETIZING FLUIDS AND THE LIKE TO THE TYMPANIC MEMBRANE

[75] Inventors: Michael W. Walsh, St. Paul; John J. Walsh, Red Wing, both of Minn.

[73] Assignee: Apdyne Medical Company, Minneapolis, Minn.

[21] Appl. No.: 902,771

[22] Filed: Jun. 23, 1992

Related U.S. Application Data

[63] Continuation of Ser. No. 571,771, Aug. 24, 1990, abandoned.

[51] Int. Cl.$^5$ .............................................. A61M 35/00
[52] U.S. Cl. ........................................................ 604/1
[58] Field of Search ........................................ 604/1-3

[56] References Cited

U.S. PATENT DOCUMENTS

| | | |
|---|---|---|
| 355,308 | 1/1887 | Foote . |
| 1,687,472 | 10/1928 | Dorman et al. ............... 604/1 |
| 1,705,256 | 3/1929 | Krusi ............................. 604/2 |
| 1,939,612 | 12/1933 | Rose . |
| 3,508,547 | 9/1967 | Deuschle . |
| 3,614,245 | 10/1971 | Schwartzman . |
| 3,818,911 | 6/1974 | Fournier . |
| 3,901,233 | 8/1975 | Grossan . |
| 3,958,571 | 5/1976 | Bennington . |
| 4,173,978 | 11/1979 | Brown . |
| 4,175,560 | 11/1979 | Knoll ............................. 604/1 |
| 4,192,300 | 3/1980 | Devers ....................... 604/1 X |
| 4,259,955 | 4/1981 | Ritter ............................ 604/1 |
| 4,283,809 | 8/1981 | Prost . |
| 4,486,109 | 12/1984 | Rosofsky ..................... 604/3 X |
| 4,540,408 | 10/1985 | Lloyd . |
| 4,586,604 | 5/1986 | Alter .............................. 604/1 |
| 4,718,889 | 1/1988 | Blasius, Jr. et al. . |
| 4,740,194 | 4/1988 | Barabino et al. . |
| 4,747,719 | 5/1988 | Parkin . |
| 4,776,835 | 10/1988 | Lee . |
| 4,778,457 | 10/1988 | York . |
| 4,799,815 | 1/1989 | Barabino et al. . |
| 4,863,422 | 9/1989 | Stanley . |
| 4,887,994 | 12/1989 | Bedford . |
| 4,913,682 | 4/1990 | Shabo . |

FOREIGN PATENT DOCUMENTS

| | | | |
|---|---|---|---|
| 0549123 | 6/1957 | Italy | 604/1 |

*Primary Examiner*—Randall L. Green
*Assistant Examiner*—Elizabeth M. Burke
*Attorney, Agent, or Firm*—Robert A. Elwell; Amy J. Hoffman; Harold D. Jastram

[57] ABSTRACT

The present invention relates to an improved applicator designed for the application of anesthetic fluids such as phenol as well as other fluid medicants to the tympanic membrane. The applicator comprises an articulating member with a finger gripping zone adjacent the proximal end thereof, and an angularly disposed fluid retaining applicator pad secured to the distal end thereof. The distal end is provided with a cylindrical fluid retaining applicator pad attached to the cross-sectional surface of the tip, with the outer diameter of the pad being generally equivalent to that of the articulating member. The fluid retaining applicator pad permits painless application of an anesthetizing fluids such as phenol to the tympanic membrane, with excellent positioning control being made possible by the finger gripping portion of the articulating member.

7 Claims, 1 Drawing Sheet

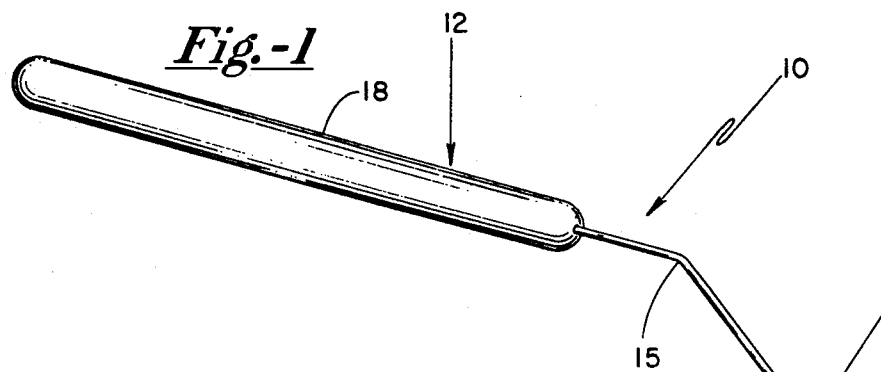
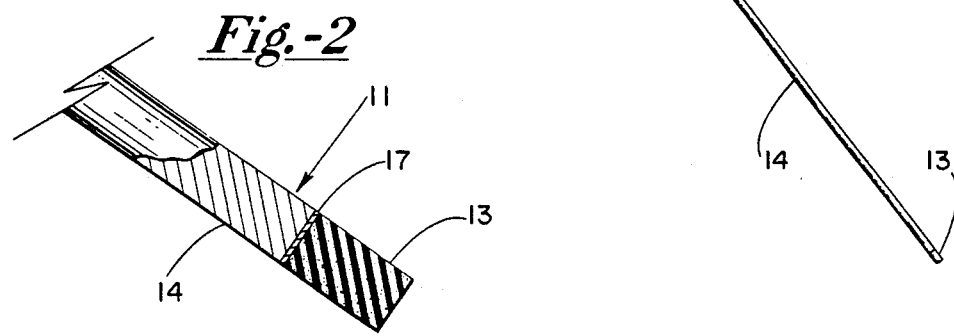
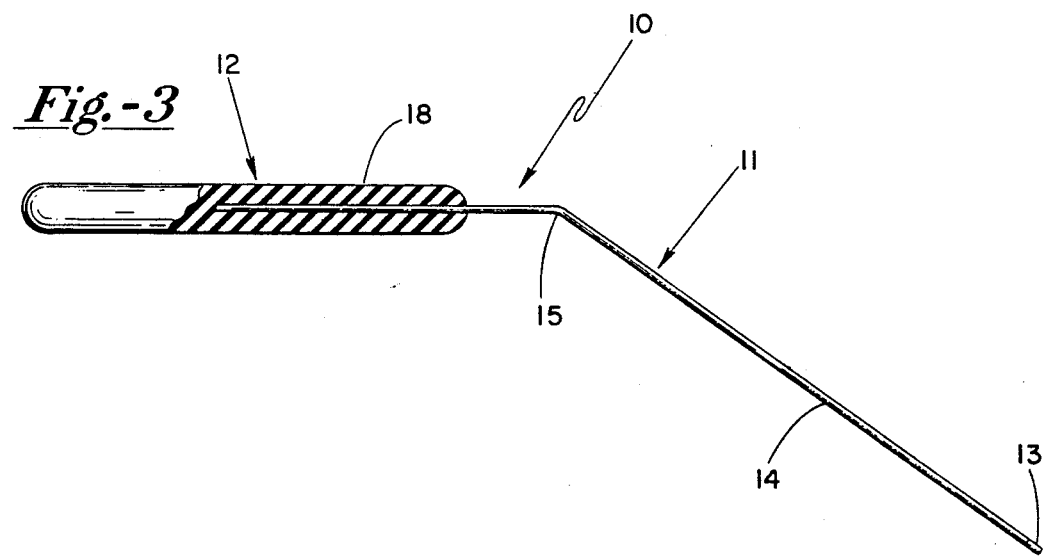

APPLICATOR MEANS FOR THE APPLICATION OF ANESTHETIZING FLUIDS AND THE LIKE TO THE TYMPANIC MEMBRANE

This is a continuation of prior application Ser. No. 07/571,771, filed Aug. 24, 1990, now abandoned.

BACKGROUND OF THE INVENTION

The present invention relates generally to an improved applicator designed for the application of anesthetizing or anesthetic fluids such as phenol or the like, as well as other medicants to the tympanic membrane. The device of the present invention comprises an articulating member with a finger gripping zone adjacent one end thereof and an angularly disposed fluid retaining applicator pad secured to the other end thereof, and with controlled positioning and movement of the pad being made possible by the design of the overall structure.

In the past, a number of techniques have been utilized for anesthetizing the tympanic membrane, and have been described in literature. These known techniques include the use of topical anesthetics, infiltration of the tissues of the ear with hypodermic injection, as well as the use of iontophoresis. By way of example, iontophoresis induces an anesthetic effect by applying a current through an anesthetic solution to the tympanic membrane with the dissolved anesthetic, then penetrating the tympanic membrane epithelium and inducing anesthesia. This technique, although effective, is time consuming in its application taking generally 20 to 30 minutes to produce anesthesia of the tympanic membrane.

Local infiltration of the ear canal is a more rapid technique, however it is associated with significant discomfort during the process of infiltration.

Many topical solutions have been used for anesthesia of the tympanic membrane. The vast majority of these solutions include phenol as their primary component. Of these topical anesthetics, pure liquefied phenol has evolved as being the preferred material or material of choice for this application.

Applicators designed for the application of phenol to the tympanic membrane are well known in the art. The applicators are of two specific types, rigid applicators and absorbent applicators.

Rigid applicators are usually constructed of a material inert to phenol and formed in such a fashion as to allow a small reservoir of phenol to adhere to the applicator. Application of the phenol is then accomplished by placing the rigid applicator in contact with the tympanic membrane and allowing the phenol to flow onto the tympanic membrane. Because of the rigid nature of these applicators, they may produce mechanical trauma to the tympanic membrane during the application of the phenol, resulting in discomfort.

Up until the present, absorbent applicators were frequently individually constructed at the time of use by merely twisting a wisp of cotton onto a shaft. These individually constructed applicators were generally of non-uniform construction and as a result, were prone to application of a non-uniform and possibly excessive quantity of phenol to the tympanic membrane. Phenol is a highly caustic substance and excessive quantities or uncontrolled application of phenol to the tympanic membrane is capable of causing serious injuries and consequences.

SUMMARY OF THE INVENTION

The present invention is directed to an applicator device having a design which is easily manufactured and which, when utilized, allows painless, well controlled application of phenol or other medicants to the tympanic membrane.

The applicator of the present invention includes an articulating member with a finger gripping zone adjacent one end thereof and an angularly disposed fluid retaining applicator pad secured to the opposed end thereof. The articulating member includes an elongated shaft with first and second angularly disposed segments, and with the first segment comprising the proximal end and having a finger gripping portion secured thereto. The second segment, which is angularly disposed to the first segment, comprises the applicator portion and has a fluid retaining pad means adhesively bonded or otherwise secured to the distal tip end, with the fluid retaining pad having an outer diameter which is generally equivalent to that of the shaft segment to which it is secured. Hot-melt adhesive, when utilized, allows rapid and efficient manufacture of the applicator, as well as the production of a secure bond between the fluid retaining foam tip and the articulating member or shaft. The articulating member is formed into two angularly disposed segments, thus permitting unobstructed visualization of the tympanic membrane during use of the applicator device. In addition, a generally concentric finger gripping handle means is attached to the proximal end of the articulating member, with this handle being preferably constructed of a material which is non-slipping, resilient, and allows gripping and control of the articulating member or shaft during use of the applicator.

Therefore, it is a primary object of the present invention to provide an improved applicator means for the application of anesthetizing fluids and the like to the tympanic membrane, and including an articulating member with proximal and distal ends, including a finger gripping zone adjacent the proximal end thereof and a fluid retaining applicator pad secured to the distal tip end thereof.

It is yet a further object of the present invention to provide an improved applicator means for the application of anesthetizing fluids and the like to the tympanic membrane, and including an articulating member with angularly disposed finger gripping and fluid applicator zones, and with pad means being secured to the finger gripping zone in order to provide non-slipping gripping and control of the articulating member or shaft during use of the applicator.

Other and further objects of the present invention will become apparent to those skilled in the art upon a study of the following specification, appended claims, and accompanying drawings.

BRIEF DESCRIPTION OF THE DRAWINGS

FIG. 1 is a perspective view of a preferred embodiment of the present invention, and illustrating the arrangement of the finger gripping handle and fluid retaining absorbent tip;

FIG. 2 is a sectional view taken through the diameter of the device and illustrating the fluid retaining pad and distal end portions of the applicator means of the present invention, with FIG. 2 being shown on a slightly enlarged scale; and FIG. 3 is a diametrical sectional view of the device, partially broken away, and illustrating the proximal end of the articulating member and finger gripping portion thereof.

DESCRIPTION OF THE PREFERRED EMBODIMENT

With attention being directed to FIG. 1 of the drawings, the preferred embodiment of the present invention is illustrated, with the applicator means generally designated 10 including an articulating member 11 with a finger gripping zone 12 adjacent the proximal end thereof, and with an angularly disposed fluid retaining applicator pad 13 being secured to the opposed or distal end thereof. The distal portion 14 is angularly offset from the proximal section or segment 12 as at 15.

Thus, the articulating member 11 comprises an elongated shaft with first and second angularly disposed segments 12 and 14, with segment 12 comprising a finger gripping portion and with the segment 14 comprising the fluid retaining applicator segment.

With attention now being directed to FIG. 2 of the drawings, the distal tip portion 14 of applicator means 10 includes, as indicated, fluid retaining pad means 13 adhesively bonded as at and along zone 17, applicator pad receiving surface, to the cross-sectional surface of segment 14. Hot-melt adhesives are, of course, widely commercially available.

With attention being directed to FIG. 3, it will be observed that the segment 12 of applicator means 10 is coated or otherwise covered with a resilient pad member 18 which is arranged generally concentrically with proximal segment 12.

THE FLUID RETAINING TIP

As indicated, the fluid retaining tip 13 is preferably fabricated from plastic foam, and is provided with a number of important properties. The plastic foam is of open-cell configuration so as to be absorbent, and is inert to phenol as well as other medicants. The structural properties of the material are such that the tip is rigid when dry to facilitate shaping and attachment to the articulating member or shaft during the manufacturing process, and sufficiently soft and flexible when medicant is absorbed into the tip. This flexibility permits non-traumatic application of the medicant to the tympanic membrane. A number of materials are available to provide suitable foam tips. One such material is melamine-based foam of open-cell configuration, it being understood that other flexible, inert, open-cell, polymer foam materials such as polypropylene and polyurethane may be successfully utilized. Preferably, when melamine-based foam is utilized, the density is about 1.0 pounds per cubic foot (0.015 grams per cubic centimeter). Such foams are commercially available.

THE HOT-MELT ADHESIVE

The hot-melt adhesive is selected so as to be inert to phenol and other medicants. Additionally, the adhesive has a fast cure time of approximately five seconds or less in order to provide adequate bonding and structural strength to firmly attach the tip 13 to applicator segment 14. The use of hot-melt adhesive in this embodiment is to permit appropriate bonding of tip 13, without otherwise interfering with the utilization of the device. Hot melt adhesives are, of course, commercially available.

The angular bend at 15 is preferably arranged at an angle of approximately 35°, thus allowing use of the applicator with substantially complete unobstructed view of the tip during application of the medicant to the tympanic membrane. The elongated shaft 11 is constructed of any rigid or semi-rigid material compatible with hot-melt adhesive and chemically inert to phenol and other medicants. Either steel or stainless steel may be found suitable for this purpose. The finger gripping portion 18 is composed of a flexible resilient material, and may be fabricated from silicone rubber, or alternatively of a natural rubber or low durometer moldable thermoplastic material.

It will be appreciated, of course, that other embodiments of the present invention may be prepared without departing from the spirit and scope of the present invention.

What is claimed is:

1. A tympanic membrane applicator for application of anesthetizing fluid to a tympanic membrane of a patient, the applicator comprising:
    an articulating member including:
        a first elongated segment having a distal end, a proximal end, and a proximally located finger gripping portion having a gripping means secured thereto,
        a second elongated segment having a first end and a second end, the first end of the second segment angularly connected to the distal end of the first segment and the second end having a cross-sectional surface defining a swab pad receiving surface; and
    a cylindrical fluid retaining applicator swab pad adhesively secured by an end of the pad to the swab pad receiving surface, and wherein the cylindrical pad and the second elongated segment have equivalent diameters and are co-aligned and wherein the applicator is sized to fit within a human ear canal such that a user has an unobstructed view of the tympanic membrane around the applicator during use.

2. A tympanic membrane applicator for applying anesthetizing fluids to a tympanic membrane of a patient, the tympanic membrane applicator including:
    an articulating member comprising an elongated shaft with first and second angularly disposed segments, said first segment having a distal end and a proximal end with a finger gripping zone adjacent the proximal end of said first segment, and said second segment having a proximal end connected to the distal end of the first segment and a distal tip, the distal tip of said second segment having a cross-sectional surface defining an applicator swab pad receiving surface; and an applicator swab pad, the pad having a cylindrical configuration with a cross-sectional surface equal to the applicator swab pad receiving surface, and secured, in a concentric arrangement, by an end of the swab pad to the applicator swab pad receiving surface and wherein the applicator is sized to fit within a human ear canal such that a user has an unobstructed view of the tympanic membrane around the applicator during use.

3. The applicator means as defined in claim 2 wherein said applicator swab pad is a flexible, inert, open-cell, polymer foam.

4. The applicator as defined in claim 2 and wherein said first and second angularly disposed segments are arranged at an angle of approximately 35°.

5. The applicator of claim 2 and wherein the finger gripping zone includes a gripping pad means fabricated from silicone rubber.

6. A tympanic membrane applicator for applying anesthetizing fluids to the tympanic membrane of a patient, the tympanic membrane applicator comprising:

an articulating member comprising an elongated shaft with first and second angularly disposed segments, the articulating member having a proximal end and a distal end, the distal end of the articulating member having a cross-sectional surface, with a finger gripping zone adjacent the proximal end of said articulating member, said finger gripping zone having a peripherally secured gripping pad means and with the gripping pad means being arranged concentrically with said first segment and an applicator swab pad receiving surface at the cross-sectional surface of the distal end; and a cylindrical fluid retaining applicator swab pad of a melamine-based open-cell foam secured at an end of the cylindrical pad to the applicator swab pad receiving surface, said applicator swab pad receiving surface and said swab pad having equal outer diameters and wherein the applicator is sized to fit within a human ear canal such that a user has an unobstructed view of the tympanic membrane around the applicator during use.

7. The applicator as defined in claim 6 wherein said melamine-based open-cell foam has a density of about 1 pound per cubic foot.

* * * * *